United States Patent [19]

Giuliani et al.

[11] Patent Number: 4,513,087

[45] Date of Patent: Apr. 23, 1985

[54] REVERSIBLE OPTICAL WAVEGUIDE VAPOR SENSOR

[75] Inventors: John F. Giuliani, Kensington, Md.; Henry Wohltjen, Burke, Va.

[73] Assignee: The United States of America as represented by the Secretary of the Navy, Washington, D.C.

[21] Appl. No.: 462,493

[22] Filed: Jan. 31, 1983

[51] Int. Cl.³ .................... G01N 21/00; G01N 21/78
[52] U.S. Cl. .................................... 436/96; 422/57; 422/58; 422/86; 422/91; 436/111; 436/113; 436/165
[58] Field of Search .................. 422/57, 58, 86, 91; 436/96, 106, 111, 164, 165, 113; 356/73.1

[56] References Cited

U.S. PATENT DOCUMENTS

| | | | |
|---|---|---|---|
| 3,617,136 | 11/1971 | Lyshkow | 356/180 |
| 3,998,591 | 12/1976 | Eckfeldt | 422/91 X |
| 4,050,895 | 9/1977 | Hardy et al. | 422/86 X |
| 4,106,909 | 8/1978 | David et al. | 436/113 |
| 4,294,513 | 10/1981 | Nelson et al. | 350/96.29 |
| 4,447,546 | 5/1984 | Hirschfeld | 422/57 X |

OTHER PUBLICATIONS

Kuznetsova et al., Chemical Abstracts, vol. 95, No. 95:96543q (1981).

Drexhage, "Chemical Abstracts", vol. 87, No. 87:175066z, 1977.

Standardization in Spectrophotometry and Luminescence Measurements, Proceedings of a Workshop Seminar held at the National Bureau of Standards, Gaithersburg, Md.-Nov. 19, 20, 1975.

E. E. Hardy et al., "Coated Optical Guides for Spectrophotometry of Chemical Reactions" Nature 257, 666-667 (Oct. 23, 1975).

D. J. David et al., "Direct Measurement of Ammonia in Ambient Air" Analytical Letters 9 (4), 389-404 (1976).

Primary Examiner—Arnold Turk
Assistant Examiner—Robert J. Hill, Jr.
Attorney, Agent, or Firm—Robert F. Beers; William T. Ellis; Alan P. Klein

[57] ABSTRACT

A device for detecting small amounts of a chemical such as ammonia, and other ammonia-like molecules such as hydrazine or pyridine, in air and in other gases is disclosed. A capillary tube serves as a multiple total reflective medium for an optical beam from a light-emitting diode. The outer surface of the capillary tube is coated with a dye which, when exposed to the chemical, changes color so that the multiply reflected light is modified. The resultant change in the output light intensity from the capillary tube is photodetected and recorded to sense the presence of the chemical. When the chemical is removed, the dye returns to its original color so that the device can be reused.

21 Claims, 1 Drawing Figure

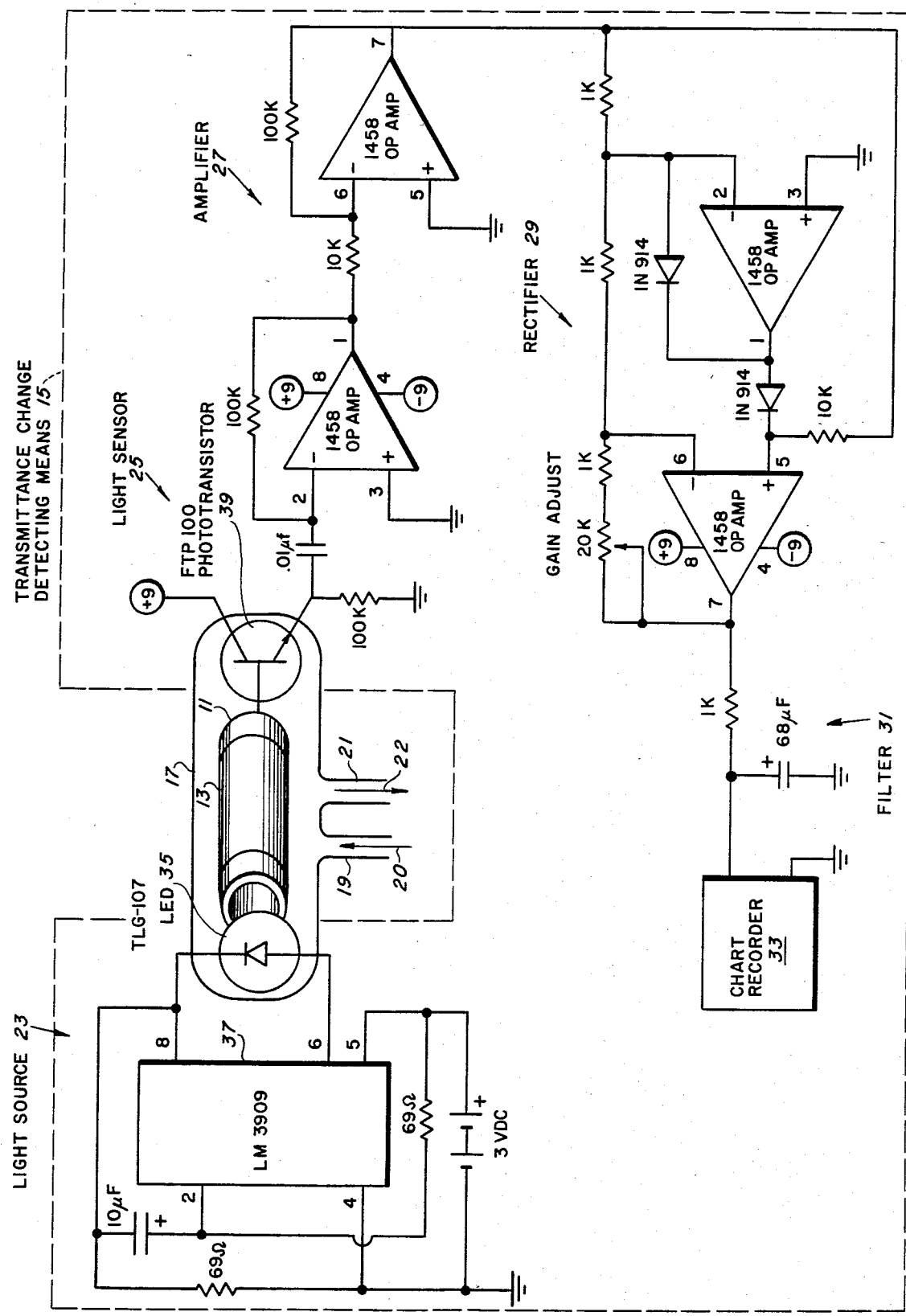

REVERSIBLE OPTICAL WAVEGUIDE VAPOR SENSOR

BACKGROUND OF THE INVENTION

The present invention relates to vapor sensors, and more particularly to such sensors using optical elements.

The development of reversible devices—devices which can be reused—for detecting toxic gases such as ammonia and hydrazine, is currently an active area of research.

The first description of a device utilizing an organic film-coated optical waveguide for vapor detection was published in *Nature*, Vol. 257, p.666 in 1975 by Hardy, David, Kapany, and Unteilertner. These authors used the chemical reaction between cyanide ions and a picrate dye film coating on the surface of a light-guiding quartz rod to detect the presence of the cyanide ions. The chemical reaction between the cyanide ions and the coating changes the refractive index and absorption coefficient of the coating. The resulting chamber in light transmission through the rod is proportional to the concentration of the cyanide species. Subsequently, Hardy, David, Willson, and Ruffin described in *Anayltical Letters* Vol. 9, p. 389 (1976), a similar device incorporating a ninhydrin-coated quartz rod which could detect ammonia vapor concentrations of below 100 ppb. For both of these devices however, the dye reactions are chemically irreversible and hence the devices are of limited practical use.

SUMMARY OF THE INVENTION

Accordingly, it is an object of the invention to detect small amounts of a chemical in air and in other gases.

Another object is to provide a device for such purpose which can be used repeatedly without permanent degradation.

These and other objects of the invention are achieved by an oxazine perchlorate device which includes an optical waveguide, a dye film coated on the waveguide, and means for detecting a change in the optical trasmittance of the waveguide. The dye film has the property of changing from its normal color to another color when exposed to a chemical, wherein the chemical is ammonia, hydrazine, or pyridine and returning to its original color when the chemical is removed. The optical transmittance of the waveguide varies with the color of the dye film coating, thereby providing a sensitive indicator of the presence of the chemical.

One advantage and unique feature of the device is its relatively rapid reversible response to wide ranges of chemical concentrations at room temperature without permanent degradation of the dye film. Another advantage is that the transmittance change-detecting means can be made compact in size through the use of the latest developments in solid state microelectronic technology, i.e. small LED's phototransistors, operational amplifiers etc. The device has the capability of being further scaled down using the techniques of integrated optics and electronics without losing its detection capabilities. Use of a capillary tube for the optical waveguide in one embodiment allows the optical beam to reflect on itself many times. This results in sensitivity to wide optical transmittance changes which is enhanced many times over then when conventional cylindrical rods are used. Lastly, the device consists of readily available and inexpensive components.

Additional advantages and features will become apparent as the subject invention becomes better understood by reference to the following detailed description when considered in conjunction with the accompanying drawings wherein:

BRIEF DESCRIPTION OF THE DRAWINGS

The sole FIGURE is a schematic diagram of the device of the present invention.

DESCRIPTION OF THE PREFERRED EMBODIMENT

Referring to the FIGURE, the reusable device for detecting small amounts of a chemical in air and in other gases includes an optical waveguide 11 which is coated with a dye film 13. The optical transmittance of the waveguide 11 varies with the color of the dye flm coating 13. The film 13 has the property of changing from its normal color when exposed to the chemical to be detected and of returning to its original color when the chemical is removed. A transmittance change-detecting means 15 is provided to detect the corresponding change in the optical transmittance of the waveguide 11.

While the optical waveguide 11 may take a variety of forms, conveniently it may take the form shown in the FIGURE of a glass capillary tube. A capillary tube configuration is desirable because its geometry allows a significantly greater number of optical reflections to be maintained between the glass-film interface close to the critical angle than does a rod, for example. It is estimated that greater than 600 optical reflections can take place along a 90 mm×1.1 mm (OD)×0.8 mm (ID) commercially available soda-glass capillary tube. The multiple internal reflections enhance the sensitivity by causing a large change in the light transmitted when a small change occurs in the optical characteristics at the surface of the dye film-coated capillary tube.

While the material of the dye film may take a variety of forms, when the chemical to be detected is an ammonia-like compound such as ammonia ($NH_3$), hydrazine ($NH_2$), or pyridine ($NCH(CHCH)_2$) the dye film may conveniently take the form of an oxazine perchlorate dye. This dye is described by D. H. Drexhage in "Fluorescence Efficiency of Laser Dyes", *National Bureau of Standards Special Publication*, Vol. 466, p. 33 (issued May 1977), whose disclosure is incorporated by reference. Such a dye film may be formed by first acid cleaning and etching the surface of the glass capillary tube for 2 minuts in a buffered solution of hydrogen fluoride (HF) solution, and then spraying the surface with a $10^{-5}$ molar oxazine perchlorate-in-ethanol solution. The dye solution quickly dries, leaving a surface film which is less than a micron thick and granular in appearance.

A cell 17 surrounds the optical waveguide 11 and has inlet means 19 for transporting gas into the cell (in the direction of arrow 20) and outlet means 21 for withdrawing the gas from the cell (in the direction of arrow 22). The cell may comprise a glass jacket sealed by two neoprene stoppers. This allows the gas to freely circulate over the entire surface of the film-coated optical waveguide.

While the transmittance change-detecting means 15 may take a variety of forms, conveniently it may take the form shown in the FIGURE of a light source 23 disposed at one end of the optical waveguide 11, a light sensor 25 disposed at the other end of the waveguide, an amplifier 27 connected to the light sensor; a rectifier 29 connected to the amplifier; a filter 31 connected to the rectifier; and a DC strip chart recorder 33 connected to the filter.

The light source 23 may include, for example, a 560 nm light-emitting-diode 35 (TGL-107) to which is connected a light flasher 37. The light sensor 25 may include, for example, a phototransistor 39 (FTP-100). The LED 35, coated capillary tube 11, and phototransistor 39 may all be supported in the cell 17. The electronics may be implemented with conventional integrated circuits occupying a few square inches of space on a small printed circuit board and be battery-powered. The simplicity and ruggedness of such an apparatus is appropriate for portable applications.

In operation, a gas to be tested is transported through the inlet means 19 into the cell 17. The flasher 37 produces 560 nm light pulses from the LED 35 and the latter transmits the pulses through the capillary tube 11. The light is multiply reflected along the inside of the circular capillary wall producing an annular light pattern at the phototransistor 39. The phototransistor 39 converts the light pulses to electrical pulses which are amplified by the amplifier 27, rectified by the rectifier 29, smoothed by the filter 31, and recorder as a direct current signal by the chart recorder 33.

When a carrier gas containing the chemical to be detected is admitted to the cell 17, the dye film 13 quickly changes color (from blue to red in the case of an oxazine perchlorate dye film exposed to an ammonia-like compound). The color change causes a change in the optical transmittance of the capillary tube 11 and a resultant change in the intensity of the light pulses received by the phototransistor 39. The change in the light pulse intensity causes a proportional change in the direct current signal at the chart recorder 33, thereby indicating the presence of the chemical.

When the gas containing the chemical is withdrawn from the cell 17 and replaced by uncontaminated ambient air, the dye film 13 rapidly changes back to its original color (from red to blue in the previous example of an oxazine perchlorate dye film). The accompanying change in the optical transmittance of the capillary tube 11 causes the direct current signal at the chart recorder 33 to decay back to the baseline observed prior to admitting the chemical to the cell 17. It has been observed that the reversibility of color change is independent of ammonia concentration levels in the case of an oxazine perchlorate dye film exposed to ammonia.

A calibration curve can be plotted by recording the logarithm of the changes in optical transmittance at 560 nm (the waveguide of the LED 35) as a function of the logarithm of the changes in the chemical concentration. Once calibrated, an absolute measurement of the concentration of the chemical in the carrier gas is possible. For example, ammonia vapor concentrations from 1000 ppm to less than 60 ppm have been easily and reproducibly detected. Reference may be had to the article "Reversible Optical Waveguide Sensor for Ammonia Vapors" by J. F. Giuliani, H. Wohltjen and N. L. Jarvis in *Optics Letters* Vol. 8, No. 1 pp. 54–56 (Jan. 1983), herein incorporated by reference, for a further descussion of test results.

Thus, there has been described a detection device having a relatively rapid reversible response to wide ranges of chemical concentration is air or in other gases.

Obviously many modifications and variations of the present invention are possible in light of the above teachings. It is therefore to be understood that within the scope of the appended claims the invention may be practiced otherwise than as specifically described.

What is claimed as new and desired to be secured by Letters Patent of the United States is:

1. In combination,
an optical waveguide; and
an oxazine perchlorate dye film coated on the optical waveguide and having the property of changing from its normal color to another color when exposed to a chemical selected from the group consisting of ammonia, hydrazine, and pyridine, and returning to its original color when the chemical is removed;
whereby the optical transmittance of the waveguide varies with the color of the dye film coating.

2. The combination recited in claim 1 wherein:
the optical waveguide is a capillary tube.

3. The combination recited in claim 2 wherein:
the material of the capillary tube is glass.

4. The combination recited in claim 3 wherein:
the dye film is formed by spray-coating the capillary tube with $10^{-5}$ molar oxazine perchlorate-in-ethanol solution.

5. The combination recited in claim 4 including
a cell surrounding the capillary tube, wherein the cell has an inlet means for transporting gas into the cell, and an outlet means for withdrawing gas from the cell.

6. A reusable device for detecting small amounts of a chemical selected from the group consisting of ammonia, hydrazine, or pyridine in air and in other gases comprising:
an optical waveguide;
an oxazine perchlorate dye film coated on the optical waveguide and having the property of changing from its normal color to another color when exposed to the chemical and returning to its original color when the chemical is removed, the optical transmittance of the waveguide varying with the color of the oxazine perchlorate dye film coating; and
means for detecting a change in the optical transmittance of the waveguide.

7. The device of claim 6 wherein:
the optical waveguide is a capillary tube.

8. The device recited in claim 7 wherein the capillary tube has two ends, and the transmittance change-detecting means includes:
a light source disposed at one end of the capillary tube for transmitting light pulses through the tube.

9. The device recited in claim 8, wherein the transmittance change-detecting means includes:
a light sensor disposed at the other end of the capillary tube for receiving the light pulses and converting them to electrical pulses.

10. The device recited in claim 9 wherein the transmittance change-detecting means includes:
an amplifier connected to the light sensor for amplifying the electrical pulses.

11. The device recited in claim 10 wherein the transmittance change-detecting means includes:
a rectifier connected to the amplifier for rectifying the amplified pulses.

12. The device recited in claim 11 wherein the transmittance change detecting means include:

a filter connected to the rectifier for smoothing the output signal from the rectifier.

13. A reusable device for detecting small amounts of ammonia, hydrazine and pyridine in air and in other gases comprising:
    a capillary tube having two ends;
    an oxazine perchlorate dye film coated on the capillary tube and having the property of changing from its normal color to another color when exposed to a chemical selected from the group consisting of ammonia, hydrazine, and pyridine, and returning to its original color when the chemical is removed, the optical transmittance of the capillary tube varying with the color of the dye film coating;
    a light source disposed at one end of the capillary tube for transmitting light pulses through the capillary tube;
    a light sensor disposed at the other end of the capillary tube for receiving the light pulses and converting them to electrical pulses;
    an amplifier connected to the light sensor for amplifying the electrical pulses;
    a rectifier connected to the amplifier for rectifying the amplified pulses;
    a filter connected to the rectifier for smoothing an output signal from the rectifier; and
    a recorder connected to the filter for recording the smoothed signal.

14. The device recited in claim 13 wherein:
    the material of the capillary tube is glass.

15. The device recited in claim 14 including:
    a cell surrounding the capillary tube, the cell having an inlet means for transporting gas into the cell, and an outlet means for withdrawing gas from the cell.

16. The device recited in claim 15 wherein the light source includes:
    a light-emitting diode.

17. The device recited in claim 16, wherein the light sensor includes:
    a phototransistor.

18. The device recited in claim 17 wherein the light source includes:
    a flasher connected to the light-emitting diode for producing light pulses from the light-emitting diode.

19. A reusable device for detecting small amounts of ammonia, hydrazine and pyridine in air and in other gases comprising:
    a glass capillary tube having two ends;
    an oxazine perchlorate dye film coated on the capillary tube by spray-coating the capillary tube with a $10^{-5}$ molar oxazine perchlorate-in-ethanol solution and having the property of changing from its normal color to another color when exposed to a chemical selected from the group consisting of ammonia, hydrazine, and pyridine, and returning to its original color when the chemical is removed, the optical transmittance of the capillary tube varying with the color of the oxazine perchlorate dye film coating;
    a cell surrounding the capillary tube;
    inlet means for transporting gas into the cell;
    outlet means for withdrawing gas from the cell;
    a light source, including a light-emitting diode and a flasher connected to the light emitting diode, the light source disposed at one end of the capillary tube for transmitting light pulses through the capillary tube;
    a light sensor including a phototransistor disposed at the other end of the capillary tube for receiving the light pulses and converting them to electrical pulses;
    an amplifier connected to the light sensor for amplifying the electrical pulses;
    a rectifier connected to the amplifier for rectifying the amplified pulses;
    a filter connected to the rectifier for smoothing an output signal from the rectifier; and
    a recorder connected to the filter for recording the smoothed signal.

20. A reusable method of detecting small amounts of a chemical selected from the group consisting of ammonia, hydrazine, or pyridine in a gas comprising the steps of:
    transmitting light through an optical waveguide coated with an oxazine perchlorate dye film whose normal color changes to another color when exposed to the chemical and which returns to its original color when the chemical is removed;
    circulating the gas having the chemical therein over the waveguide such that the chemical comes into contact with the oxazine perchlorate dye film; and
    detecting changes in the optical transmittance of the waveguide caused by variation in the color of the dye film.

21. The method recited in claim 25 wherein:
    the dye film is formed by spray-coating the optical waveguide with $10^{-5}$ molar oxazine perchlorate-in-ethanol solution.

* * * * *